Figure 1:
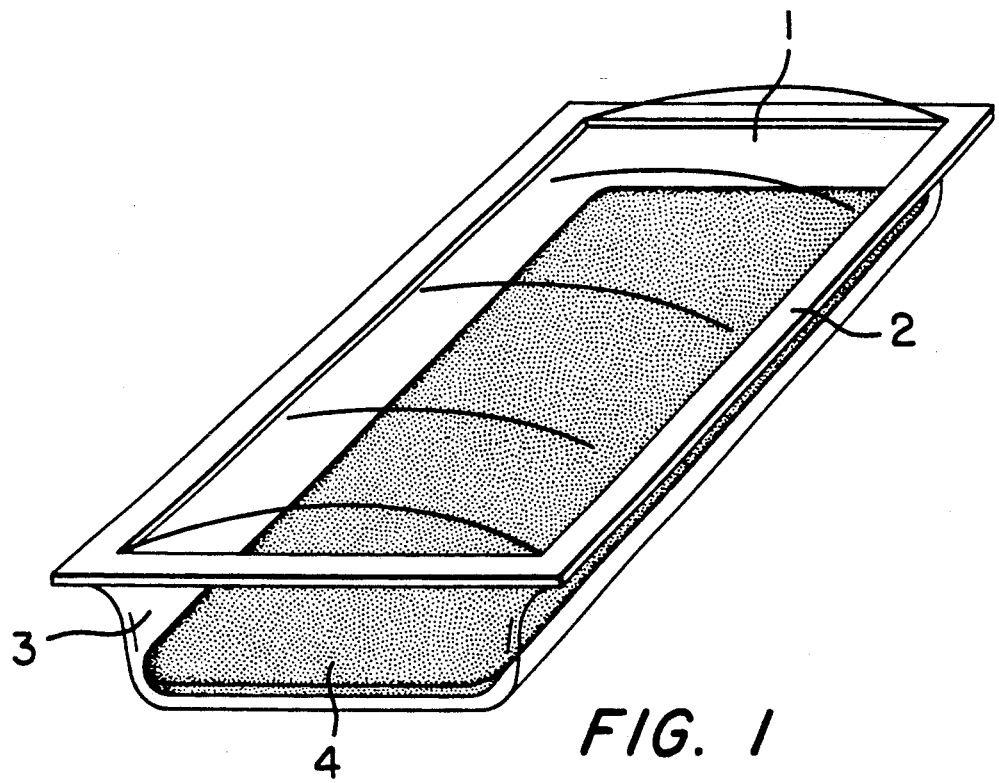

United States Patent [19]
Bergmann et al.

[11] Patent Number: 5,309,649
[45] Date of Patent: May 10, 1994

[54] PROCESS AND CONTAINER FOR FREEZE DRYING UNDER STERILE CONDITIONS

[75] Inventors: Thomas Bergmann, Penzberg; Herbert Brustmann, Tutzing, both of Fed. Rep. of Germany

[73] Assignee: Boehringer Mannheim GmbH, Mannheim-Waldhof, Fed. Rep. of Germany

[21] Appl. No.: 940,050

[22] Filed: Sep. 3, 1992

Related U.S. Application Data

[62] Division of Ser. No. 782,672, Oct. 25, 1991, abandoned, which is a division of Ser. No. 353,746, May 17, 1989, abandoned.

[30] Foreign Application Priority Data

May 26, 1988 [DE] Fed. Rep. of Germany ....... 3817906

[51] Int. Cl.$^5$ .............................................. F26B 13/30
[52] U.S. Cl. ........................................ 34/284; 34/402; 34/201; 34/92
[58] Field of Search ........................... 34/5, 92, 15, 201

[56] References Cited

FOREIGN PATENT DOCUMENTS 995930 6/1965 United Kingdom .................... 34/9

*Primary Examiner*—Henry A. Bennet
*Attorney, Agent, or Firm*—Felfe & Lynch

[57] ABSTRACT

The present invention provides a process for freeze drying of especially biologically or pharmaceutical material under sterile conditions, wherein the material to be dried is introduced into a container the sides of which consist at least partly of a hydrophobic, porous, micro-organism-impermeable, water vapor-permeable membrane, the container is tightly closed and the material is subsequently freeze dried in the closed container under the usual conditions. The present invention also provides a container for freeze drying materials under sterile conditions, wherein the sides of the container consist at least partly of a hydrophobic, porous, germ-impermeable, water vapor-permeable membrane.

12 Claims, 1 Drawing Sheet

PROCESS AND CONTAINER FOR FREEZE DRYING UNDER STERILE CONDITIONS

This is a divisional application of application Ser. No. 07/782,672, filed Oct. 25, 1991, now abandon; which in turn is a divisional of application Ser. No. 07/353,746, field May 17, 1989, now abandoned.

FIELD OF THE INVENTION

The present invention is concerned with a process for freeze drying under sterile conditions, as well as with a container for the carrying out of the process. The present invention is especially concerned with the drying of biological and/or pharmaceutical material.

BACKGROUND OF THE INVENTION

In the case of biological and pharmaceutical materials, it is frequently necessary to store the materials completely dry until they are used. These sensitive substances are mostly only obtainable by freeze drying. Furthermore, as a rule, it is necessary to keep these substances completely free from micro-organisms not only because of the decomposition of biological substances brought about by micro-organisms but also in order to prevent possible infections in the case of their use.

The freeze drying of biological and pharmaceutical materials is generally known (see also Ullmanns Enzyklopadie der Technischen Chemie, 3rd edition, Vol. I, p. 556 et seq.). In order to avoid a contamination of the dried material with micro-organisms and other contaminants, laborious apparatus and process-technical measures have to be made.

In the case of drying pharmaceutical preparations in ampoules or small bottles, the procedure is, for example, to provide small bottles which contain the frozen material with a bacterial filter and to dry the material in the small bottles in a first drying step to such an extent that the sublimation of the frozen solvent is concluded.

Subsequently, in a second drying stage, i.e. the so-called post or residual drying, the still remaining residual moisture is removed from the material. Since this second drying step is usually carried out in a special apparatus, the ampoules or vials must be removed from the first drying apparatus in a further working step which is prone to contamination and introduced into the second drying apparatus. For this purpose, the bacterial filter is removed and replaced by an aluminium cap provided with a rubber diaphragm and a hollow needle. After a residual drying for several days depending upon the nature of the material to be dried, the drying chamber is filled with an inert gas and with slight overpressure and the diaphragm opening closed as vapour-tightly as possible by a grouting mass.

Since the speed of sublimation in the case of this type of freeze drying is only about half as great as that of openly spread out material, the freeze drying of biological and pharmaceutical material is also carried out on plates under sterile conditions. A solution of the material to be dried is thereby first sterilised, for example by filtration over a sterile filter, subsequently poured under sterile conditions on to plates and freeze dried by means of known methods. However, a prerequisite of this process is that the whole of the freeze drying plant can be sterilised. Furthermore, it is also necessary to keep the surroundings of the drying plant free from micro-organisms.

After drying has taken place, it is necessary to remove the material in the drying plant itself or in its surroundings with mechanical processes from the plates under sterile conditions and to fill it into also sterile storage containers. This process requires laborious plant and sterile chambers, as well as an especially careful working with the material to be dried or already dried until it is confectioned ready for use.

OBJECT OF THE INVENTION

It is an object of the present invention to overcome the above-mentioned disadvantages and to provide a simple process with the help of which freeze dried material can be obtained without the above-mentioned laborious sterility requirements for the drying plant, as well as for the space surrounding this.

DESCRIPTION OF THE INVENTION

Thus, according to the present invention, there is provided a process for freeze drying of especially biological or pharmaceutical material under sterile conditions, wherein the material to be dried is introduced under sterile conditions into a container, the sides of which consist at least partly of a hydrophobic germ-impermeable, porous, micro-organism-impermeable membrane which is permeable to water in vapour form, the container is closed micro-organism-impermeably and tightly, especially cemented or welded, and the material is subsequently freeze dried directly in the closed container under the usual conditions.

The present invention is based on the surprising finding that, contrary to expectations, the vapour flow resulting by the sublimation of solvent molecules, which flows from the material to be dried to a condenser, is hindered only to a small extent by the membrane used in the process according to the present invention. Thus, surprisingly, the freeze drying of material which is enclosed by the membrane proceeds almost equally quickly as the freeze drying of the same material when open and non-packed.

The membranes used according to the present invention are hydrophobic membranes which contain pores which, on the one hand, are permeable for water vapour but, on the other hand, are so small that micro-organisms can no longer pass through. Such pores preferably have a size of $<0.5$ $\mu$m. and especially of $<0.2$ $\mu$m. According to the present invention, membranes are preferably used which, under the particular process conditions, are also tearproof even in a wet state. However, the process according to the present invention can also be carried out with less stable membranes provided that these are strengthened with a carrier material or are not excessively mechanically stressed.

The particularly selected proportion of the membrane on the wall surface of the container used in the process according to the present invention depends upon the particular selected conditions and the drying period and can easily be ascertained by means of simple experiments. In one embodiment preferred according to the present invention, the whole wall surface consists of the membrane film and in a further preferred embodiment about one half of the wall surface consists of the membrane film. Surprisingly, the process according to the present invention can also be advantageously carried out when the wall surface also only consists of up to 10% of the membrane film.

In particular, there can be used semi-permeable papers of cellulose and usual cellulose derivatives, such as cellulose acetate. According to the present invention, membranes of films of polymer compounds, for example polytetrafluoroethylene or polypropylene, can also be advantageously used. Films of sterilisation paper according to German In dustrial Standard DIN 58 953 are also quite especially useful as water vapour-permeable membranes which standard thus counts as a part of the present description. In further preferred embodiments of the present invention, Goretex and similar membranes or also commercially available film tubes can be used, such as are marketed by the firm Vihuri OY, Wipack, Finland, under the designation "Mediplast". In principle, all film membrane can be used, regardless of their components, provided that they fulfil the requirements with regard to micro-organism impermeability, air permeability and especially strength given in German Industrial Standard DIN 58 953.

Figure 2:
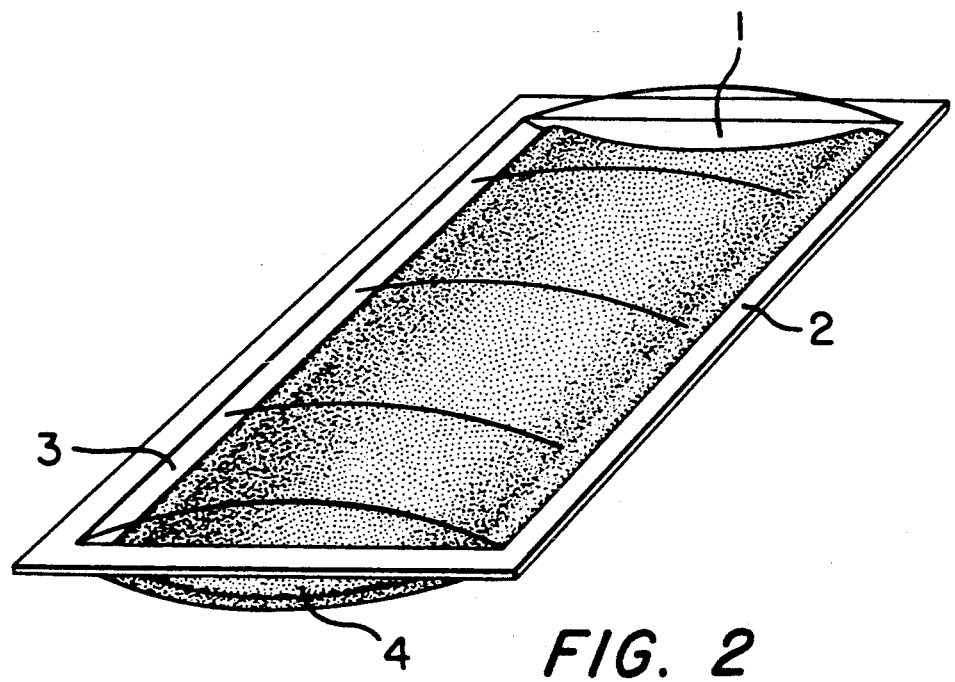

The invention will be more clearly understood with reference to the attached drawings, of which FIG. 1 is a perspective view of one preferred embodiment of the freeze drying container according to the present invention, and FIG. 2 is a perspective view of another preferred embodiment of the container according to the present invention.

In a preferred embodiment, the process according to the present invention is carried out with the use of a bag or tube, as shown in FIG. 2 of the drawings, which preferably consists of two walls 1 and 3 hermetically and tightly connected with one another on their edges 2, one wall 3 of which consists of a liquidtight material and the other wall 1 of the membrane. Reference numeral 4 identifies the material to be freeze dried in the container.

The membrane is preferably welded or glued with the vessel. According to the present invention, troughs are especially preferred as the vessels.

In a further preferred embodiment, shown in FIG. 1 of the drawings the trough consists of liquid-impermeable synthetic resin and preferably has a wall thickness of 0.5 to 1 mm.

The most favourable drying conditions, such as pressure, temperature and amount, depend upon the particular material to be dried and the thickness of the membrane, as well as upon the size and number of the pores thereof and must be determined by usual and simple experimentation for the particular material and the packing.

The following Examples are given for the purpose of illustrating the present invention:

EXAMPLE 1

The testing of the micro-organism impermeability of a membrane was so carried out according to German Industrial Standard DIN 58 953 that micro-organisms in water drops were applied to test pieces and, after drying the water drops, it was ascertained whether micro-organisms have passed through to the under side of the test pieces.

The membrane film to be tested was cut up into squares of about 50 mm. edge length and the test pieces were sterilised and dried. Each test piece of the sterilised membrane was placed on a sterilised substrate with the side which can be contaminated in the case of use upwardly and inoculated with 5 drops each of 0.1 ml. (corresponding to $10^6$ to $10^7$ micro-organisms). The test pieces were stored at a temperature of 20° to 25° C. under a relative atmospheric humidity of 40 to 60%. The drops must be completely dried within 6 hours. Each test piece was placed with the inoculated surface upwardly on the surface of a blood agar plate (1.5% agar) so that the whole film surface came into contact with the agar. After 5 to 6 seconds, the paper was removed and the plates were incubated for 16 to 25 hours at 37° C. If the agar plates treated with such film samples show no growth, the film is regarded as being sufficiently impermeable to micro-organisms. Further statements regarding the testing of the impermeability of membranes to micro-organisms and especially the preparation of test micro-organism suspensions, can be taken from part 6 of German Industrial Standard DIN 58 953.

EXAMPLE 2

A nutrient solution was produced which consisted of 10 g. peptone, 5 g. glucose, 5 g. sodium chloride, 0.084 g. monopotassium dihydrogen phosphate, 0.187 g. disodium hydrogen phosphate dihydrate and pyrogen-free water ad 1.0 liter and which had been adjusted to pH 7.0. Subsequently, it was end-sterilised in a closed, piercable bottle.

For the reception of the sterile nutrient solution to be lyophilised, there was prepared a transparent sterile bag consisting of a transparent film and an appropriate paper. For this purpose, a piece with a length of 800 mm. was cut off from a commercially available roll of transparent sterilisation bag film of the firm Wipak Medical, type Steri-King R 47 which is available in the form of a tube, i.e. is welded on both sides but is otherwise open, the roll having a width of 400 mm. This tube was welded on both of the open sides with a commercially available film-welding apparatus to form a bag. Subsequently, this bag was sterilised in an autoclave with filter programme at 123° C. and 2 bar vapour pressure, the sterile bag was placed with the transparent film downwardly for better handling in a non-sterile sheet metal trough (VA sheet metal, dimensions: length 800 mm., breadth 400 mm., height 30 mm.) and opened in a laminar flowbox under sterile conditions with disinfected scissors by cutting off of a corner. Through this opening of about 30 mm. between the film and the paper was introduced 1.5 liters of sterile nutrient solution via a sterile tube pushed into the opening. The so filled bag was again closed in the laminar flowbox under sterile conditions by means of a commercially available film welding device by welding over the corner.

The whole assembly (sheet metal trough, bag and sterile nutrient solution) was applied to a plate pre-cooled to −45° C. of a commercially available, non-sterilisable freeze drying apparatus of the firm Edwards+Kniese with a total positioning surface of 1.5 mm$^2$ and the solution frozen in. After complete freezing in of the solution under non-sterile conditions, it was freeze dried at a pressure of $10^{-1}$ mm.Hg and a plate temperature of 22° C. and the product post-dried at $10^{-3}$ mm.Hg, again under non-sterile conditions. The total drying time was about 72 hours.

The so obtained freeze-dried material, present as a pale brown powder in the transparent sterilisation bag, was subsequently introduced into a laminar flowbox and dissolved in 1.5 liters of sterile water. For this purpose, the intended puncturing point was disinfected with alcohol on the paper side, by means of a sterile canula and appropriate sterile syringe a total of 1.5 liters of sterile water was introduced into the bag, the dried material dissolved and the solution transferred into a sterile bottle. This solution was incubated for 4 days at 37° C. and subsequently the micro-organism count of the incubated solution determined by the membrane filter method.

It was shown that no micro-organisms had been entrained by the freeze drying.

We claim:

1. The method of freeze drying biological or pharmaceutical material under sterile conditions, which comprises introducing said material into a container the sides of which consist at least partly of a hydrophobic, porous, microorganism-impermeable and water vapor-permeable membrane, tightly closing the container and freeze drying said material under sterile conditions inside the closed container in a non-sterile ambient environment.

2. The method of claim 1, wherein the membrane has pores with a size of $<0.5$ μm.

3. The method of claim 2, wherein the membrane has pores with a size of $<0.2$ μm.

4. The method of claim 1, wherein said membrane is semi-permeable paper.

5. The method of claim 4, wherein the semi-permeable paper is made of cellulose or a cellulose derivative.

6. The method of claim 5, wherein a membrane of cellulose acetate is used.

7. The method of claim 1, wherein the membrane is a film of a polymer compound.

8. The method of claim 7, wherein the polymer compound is polytetrafluoroethylene or polypropylene.

9. The method of claim 1, wherein the container is in the form of a tube or bag.

10. The method of claim 9, wherein the tube or bag comprises a water-impermeable wall which is tightly connected with a further wall formed by the membrane.

11. The method of claim 1, wherein the container is a flask, ampule or vial which is closed with the membrane.

12. The method of claim 1, wherein the container is a trough which is tightly connected with the membrane as covering.

* * * * *